United States Patent
Kohno

(10) Patent No.: US 6,576,813 B2
(45) Date of Patent: *Jun. 10, 2003

(54) KNOCKOUT ANIMALS

(75) Inventor: Kenji Kohno, Nara (JP)

(73) Assignee: DNAVEC Research Inc., Ibaraki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,405

(22) PCT Filed: Jan. 30, 1998

(86) PCT No.: PCT/JP98/00408

§ 371 (c)(1),
(2), (4) Date: Nov. 18, 1999

(87) PCT Pub. No.: WO98/33899

PCT Pub. Date: Aug. 6, 1998

(65) Prior Publication Data

US 2002/0194626 A1 Dec. 19, 2002

(30) Foreign Application Priority Data

Jan. 31, 1997 (JP) ............................................. 9-033247

(51) Int. Cl.$^7$ ..................... A01K 67/00; A01K 67/027; C12N 5/00; C12N 15/00; C12N 15/63
(52) U.S. Cl. ............................ 800/18; 800/14; 800/21; 800/8; 435/320.1; 435/325; 435/455
(58) Field of Search ................................ 800/8, 14, 18, 800/21, 24, 25; 435/69.1, 320.1, 325, 455

(56) References Cited

U.S. PATENT DOCUMENTS 5,366,874 A * 11/1994 Eidels et al. ................ 435/69.1

FOREIGN PATENT DOCUMENTS

| JP | 8-322427 A | 12/1996 |
|---|---|---|
| WO | W/O 95/06723 | 3/1995 |
| WO | W/O 96/14420 | 5/1996 |

OTHER PUBLICATIONS

Iwamoto et al. Heparin–binding EGF like growth factor, which acts as the diphtheria toxin receptor, forms a complex with membrane protein DRAP27/CD9, which up–regulates functional receptors and diphtheria toxin sensitivity, The EMBO Journal vol. 13 No. 10 pp. 2322–2330, 1994.*

Monique Frain et al, Binding of a Liver–Specific Factor to the Human Albumin Gene Promoter and Enhancer, Molecular And Cellular Biology, Mar. 1990, p. 991–999, vol. 10. No. 3.*

Joseph G. Naglich et al, Expression Cloning of a Diphtheria Toxin Receptor: Identity with a Heparin–Binding EGF–like Growth Factor Precursor, Cell, vol. 69, 1051–1061, Jun. 12, 1992.*

Heyman et al., "Thymidine kinase obliteration: Creation of transgenic mice with controlled immune deficiency," *Proc. Natl. Acad. Sci. USA* 86:2698–2702 (1989).

Valdizan et al., "Induction of toxin sensitivity in insect cells by infection with baculovirus encoding diphtheria toxin receptor," *J. Biological Chemistry* 270:16879–16885 (1995).

Adachi et al., "Targeted mutation in the Fas gene causes hyperplasia in peripheral lymphoid organs and liver," *Nature Genetics* 11:294–299 (1995).

Kamps et al., "Massive targeting of liposomes, surface–modified with anionized albumins, to hepatic endothelial cells," *Proc. Natl. Acad. Sci. USA* 94:11681–11685 (1997).

Kappel et al., "Regulating gene expression in transgenic animals," *Current Opinion in Biotechnology* 3:548–553 (1992).

Viville et al., "Mouse genetic manipulation via homologous recombination," *Transgenic Animals* p. 307–321 (1997).

Wall, "Transgenic livestock: progress and prospects for the future," *Theiogenology* 45:57–68 (1996).

Walther, "Cell type specific and inducible promoters for vectors in gene theapy as an approach for cell targeting," *J. Mol. Med.* 74:379–392 (1996).

Wu and Wu, "Receptor–mediated gene delivery and expression in vivo," *The Journal of Biological Chemistry* 263(29):14621–14624 (1988).

"Diphtheria toxin binds to the epidermal growth factor (EGF)–like domain of human heparin–binding EFG–like growth factor/diphtheria toxin receptor and inhibits specifically its mitogenic activity," *Journal of Biological Chemistry*, 270(3):1015–1019 (1995).

* cited by examiner

Primary Examiner—Jeffrey Fredman
Assistant Examiner—Sumesh Kaushal
(74) Attorney, Agent, or Firm—Clark & Elbing LLP

(57) ABSTRACT

Transgenic mice are constructed by binding the "hHB-EGF/DTR" gene to the downstream of an albumin enhancer/promoter that is expressed specifically in hepatic parenchymal cells and introducing this unit into mice. After the "hHB-EGF/DTR" gene has been confirmed to be expressed specifically in hapatic cells, diptehria toxin is administered to the transgenic mice to examine whether the hepatic parenchymal cells are disrupted. The hepatic cells of the transgenic mice can be selectively dirupted depending on the administration period of the diphtheria toxin.

2 Claims, 10 Drawing Sheets

Figure 10

KNOCKOUT ANIMALS

The present application is a continued prosecution application of U.S. patent application Ser. No. 09/355,405, filed Nov. 18, 1999, which claims priority from international patent application serial No. PCT/JP98/00408, filed on Jan. 30, 1998, which, in turn, claims priority from Japanese patent application serial number JP 9/33247, filed on Jan. 31, 1997.

TECHNICAL FIELD

The present invention relates to a method to selectively disrupt a particular organ, tissue, or cell of an animal at a specific period, and an expression unit, vector, host cell, and kit that are utilized in the method. The invention also relates to a non-human animal in which a particular organ, tissue, or cell is disrupted by the method.

BACKGROUND ART

A normal function of a tissue or cell can be clarified by deleting the tissue or cell and examining the resulting effect. This procedure is performed by, for example, surgical ablation of a tissue or cell (including laser ablation) and specific expression of a toxin in a target cell (Palmiter, R. D. et al. (1987) Cell 50, 435–443; Breitman, M. L. et al. (1987) Science 238, 1563–1565; Borrelli, E. et al. (1988) Proc. Natl. Acad. Sci. USA 85, 7572–7576; Heyman, R. A. et al. (1989) Proc. Natl. Acad. Sci. USA 86, 2698–2702; Lowell, B. B. et al. (1993) Nature 3664 740–742; Ross, S. R. et al. (1993) Genes Dev. 7, 1318–1324).

When the target cells exist diffusely in the whole body, it is impossible to efficiently ablate only the target cells by the former method. When the target organ, tissue or cell is essential for normal development, the latter method results in death of the individual at embryo stage, and it is thus impossible to analyze animals after birth.

DISCLOSURE OF THE INVENTION

An objective of the present invention is to provide a method to specifically disrupt a particular organ, tissue, or cell at an arbitrary period.

Diphtheria toxin is a protein of 58 kDa and consists of two domains, fragment A and B. The fragment B domain binds to the precursor of heparin-binding EGF-like growth factor (HB-EGF)/diphtheria toxin receptor (DTR) which exists on the cell surface, and the toxin is incorporated into the cell via endocytosis. Upon fusion of the endosome with a lysosome, the conformation of the toxin is changed because of the effect of pH, and then the fragment A domain is translocated into the cytosol where the fragment inactivates peptide chain elongation factor (elongation factor 2) by ADP-ribosylating it and thus inhibits protein synthesis to bring the cell death (Honjo, T. et al. (1968) J. Biol. Chem. 243, 3553–3555; Pappenheimer, A. M. Jr. (1977) Annu. Rev. Biochem. 46, 69–94; Kohno, K. et al. (1986) Proc. Natl. Acad. Sci. USA 83, 4978–4982; Mekada, E. et al. (1988) J. Cell Biol. 107, 511–519; Moskaug, J. O. et al. (1991) J. Biol. Chem. 266, 2652–2659). The binding ability of diphtheria toxin to the precursor of HB-EGF differs among animal species. It is lower in mice than in humans or monkeys. Accordingly, a human and a monkey are sensitive to the toxin, whereas mice are not sensitive (Mitamura, T. et al. (1995) J. Biol. Chem. 270 (3), 1015–1019). Therefore, if a transgenic mouse is produced by introducing the human HB-EGF (hHB-EGF)/DTR gene inserted at the downstream of a promoter that functions specifically in a target organ, tissue, or cell so as to express the gene specifically there, the target can be disrupted at an arbitrary period by administrating diphtheria toxin to the mouse.

In fact, it has been shown that L cells, a mouse fibroblast insensitive to diphtheria toxin, become sensitive to the toxin when the hHB-EGF/DTR gene was introduced and expressed (Naglish, J. G. et al. (1992) Cell 69, 1051–1061).

The present inventors selected the enhancer/promoter of the albumin gene, which is specifically expressed in hepatic parenchymal cells (Gorski, K. et al. (1986) Cell 47, 767–776; Pinkert, C. A. et al. (1987) Genes Dev. 1, 268–276) as a specific promoter for a particular organ, tissue, or cell. The hHB-EGF/DTR gene was ligated to the downstream of the promoter, and transgenic mice were created by introducing the expression unit. Next, the inventors confirmed that the hHB-EGF/DTR gene was actually expressed specifically in the hepatic cells of the transgenic mice and examined the process of the disruption of hepatic parenchymal cells by administrating diphtheria toxin to the mice. As a result, the inventors found hepatic cells of the transgenic mice were specifically disrupted depending on the administration period of the toxin, and accomplished the present invention.

Thus, the present invention relates to a method for specifically disrupting a desired organ, tissue, or cell at a desired period by administrating a compound, and more specifically relates to:

(1) an expression unit comprising a gene encoding a receptor for a compound, which is essentially nontoxic to a host, at the downstream of a promoter functioning specifically in a particular organ, tissue, or cell, wherein said compound binds to said receptor artificially expressed in the host and shows a selective toxicity to the cell expressing said receptor;

(2) the expression unit according to (1), wherein said compound is diphtheria toxin, and said receptor for the toxin is the precursor of heparin-binding EGF-like growth factor (HB-EGF)/diphtheria toxin receptor;

(3) a vector comprising the expression unit of (1) or (2);

(4) a host cell carrying the expression unit of (1) or (2), or a vector of (3);

(5) a non-human animal carrying the expression unit of (1) or (2), or the vector of (3);

(6) a method for specifically disrupting a particular organ, tissue, or cell at a particular period in the animal of (5), wherein said method comprises administering a compound that is essentially nontoxic to the host at said particular period;

(7) the method of (6), wherein said animal is a mouse, and said compound is diphtheria toxin;

(8) a non-human animal, in which a particular organ, tissue, or cell is disrupted by the method of (6) or (7);

(9) a kit comprising the compound of (1) and a DNA comprising the expression unit of (1).

The invention relates to an expression unit comprising a DNA encoding a receptor for a compound, which is essentially nontoxic to the host, at the downstream of a promoter functioning specifically in a particular organ, tissue, or cell.

The promoter functioning specifically in a particular organ, tissue, or cell is not particularly limited. Examples of the promoter includes those of genes: the H-2 class II gene, specific for macrophages and dendritic cells; interferon α, for granulocytes; interleukins 2, 4, and 5, for T lymphocytes; insulin, for β cells in pancreas; GDNF, for glia cells; immunoglobulin, for B lymphocytes; BDNF, for neurons; HGF, for hepatic parenchymal cells; THY-1, for T lymphocytes and neurons; T-cell receptor, for T lymphocytes; and hydroxymethylglutaryl coenzyme A reductase (HMG) and factor IX, for liver.

For example, the compound that is essentially nontoxic to a host includes diphtheria toxin when the host is a mouse. The compound is not particularly limited as long as it has no toxicity in hosts into which a receptor gene is not introduced, but has a selective toxicity to a particular organ, tissue, or cell of the hosts into which a receptor gene is introduced and expressed.

The receptor for a compound that is essentially nontoxic to the host is not particularly limited as long as it exhibits toxicity to a cell expressing the receptor by binding to the compound. However, a receptor whose expression itself has a bad influence on the cell is not preferable. When the compound is diphtheria toxin, a preferable receptor is the precursor of HB-EGF (heparin-binding EGF-like growth factor)/diphtheria toxin receptor.

A form of a DNA encoding the receptor is not limited as long as it encodes the receptor protein. The DNA includes cDNA, genomic DNA, and chemically synthesized DNA, etc. The DNA encoding the receptor can be prepared by a standard method (Molecular Cloning, 2nd edition, chapters 16 and 17, Cold Spring Harbor Laboratory Press).

The DNA can be inserted at the downstream of the promoter by a standard method (Molecular Cloning, 2nd edition, chapters 16 and 17, Cold Spring Harbor Laboratory Press). The resulting product can be an expression unit of the invention.

The invention also relates to a vector comprising the above expression unit.

The vector of the present invention is not particularly limited as long as it carries a gene capable of expression in eucaryotes. The expression plasmid vector can be introduced into substantially any hosts by, for example, calcium phosphate method, DEAE-dextran method, lipofection, liposome method, HVJ membrane fusion liposome method, microinjection, particle gun technique, and electroporation. In addition, a variety of retrovirus vectors which have host-selective infectivity can be utilized. Adenovirus vector, adeno-associated virus vector, herpes virus vector, HIV vector, and sindbis virus vector are also utilized.

The expression unit can be introduced into the vector of the present invention by treating a desired nucleic acid fragment with a desired restriction enzyme to make a cohesive end at a unique restriction site and by ligating the fragment with a compatible vector fragment (Molecular Cloning, 2nd edition, chapters 16 and 17, Cold Spring Harbor Laboratory Press).

The invention also relates to a host cell carrying the above vector.

A variety of animal cells can be used, without limitation, as a host cell, into which the vector of the present invention is introduced.

The vector can be introduced into host cells by, for example, chemical methods such as calcium phosphate method (Molecular Cloning, 16.32, Cold Spring Harbor Laboratory Press (1989)), DEAE-dextran method (Molecular Cloning, 16.41, Cold Spring Harbor Laboratory Press (1989)), lipofection (Annu. N.Y. Acad. Sci. 716, 23–34 (1994)), and liposome method (Annu. N.Y. Acad. Sci. 716, 144–153 (1994)), for example. In addition, a gene carrier system utilizing polycations, such as polylysine, conjugated with a protein or sugar has been recently studied (J. Controlled Release 19, 269–274 (1992)). Physical methods can also be used and include microinjection, by which a nucleic acid is directly injected into cells (Hypertension 22, 599–607 (1993)); particle gun technique, by which a gold particle covered with a nucleic acid is shot through target cells (Proc. Natl. Acad. Sci. USA 87, 9568 (1990)); and electroporation (Cancer Treat Rev. 20, 105–115 (1994)). However, any of the above methods is incapable of integrating an introduced gene into chromosomes, and it is thus difficult to obtain long-term retaining or expression of the gene. Preferably, a vector is prepared to contain an appropriate element for retaining a nucleic acid in host cells for sufficient time so that the nucleic acid can be inserted into a desired site. Such a vector is able to enter into higher eucaryotic cells, and preferably to be integrated into chromosomes. A vector which is contained as an extrachromosomal DNA can also be used as long as it has ability to express a receptor-encoding foreign gene for a desired period. Specific examples of the vector are recombinant virus vectors, including those derived from adenovirus, retroviruses, and adeno-associated virus. Alternatively, a foreign gene can be introduced into a desired chromosomal site or nucleic acid region by using integrase and a protein that recognizes a specific DNA sequence (Science 267, 1443–1444 (1995)).

Moreover, the present invention relates to a non-human animal, carrying the above expression unit or vector, and a method for disrupting a particular organ in the animal by administering a compound. The animal of the invention is characterized by specifically expressing a receptor for the above compound in a particular organ, tissue, or cell depending on the function of an introduced promoter. Therefore, when the compound is administered into a non-human animal of the invention, the compound showed toxicity in a particular organ, tissue, or cell through binding to a receptor that is specifically expressed in the particular site. It is thus possible to specifically disrupt a particular organ in the animal depending on the administration period of the compound. The administration period is not particularly limited, but is preferably a period when the compound concentration in blood sufficiently exceeds the half saturation concentration of a receptor for a compound that is essentially nontoxic to the hosts.

The non-human animal can be generated by a known method for generating transgenic animals. For example, the method includes a method of directly injecting a gene into the pronucleus of a fertilized egg using a micropipet under a phase contrast microscopy (microinjection; Proc. Natl. Acad. Sci. USA 77, 7380–7384 (1980)), a method using a recombinant retrovirus vector (retrovirus method; Proc. Natl. Acad. Sci. USA 82, 6148–6152, 6927–6931, 8587–8591 (1985)), and a method using an embryonic stem cell (ES cell) (Proc. Natl. Acad. Sci. USA 83, 9065–9069 (1986)). The non-human animal of the present invention is basically generated by a method of generating transgenic mice, which includes three known methods (Hogan, B. et al. A manual for mouse embryo manipulation, Kindai Shuppan, Tokyo (1989); Nomura, T. et al. A laboratory manual for developmental technology, Kodansya, Tokyo (1987); and Yamamura, K. Molecular Medicine in Mice, Nankodo Co., Ltd., Tokyo (1993)). Specifically, transgenic mice can be generated by, for example, harvesting fertilized eggs, injecting an isolated gene into the pronuclei of the eggs using a micromanipulator, and then transplanting the obtained eggs into a uterine tube. Alternatively, transgenic mice can be generated by introducing a desired gene into an ES clone by electroporation, selecting desired cells in terms of drug resistance, injecting the selected cells into fertilized eggs using a micromanipulator to create chimera embryos.

Because of tissue- and cell-specific function of the gene promoter, the generated non-human animal can be used as a pathological model of a disease originating from a particular cell, specifically a model animal of diabetes or neuropathy. It can also be used as a model animal for studying the mechanism of memory by depleting neurons involved in memory at a particular developmental stage. In addition, minituarized animals can be generated by arresting the animal growth at a desired period.

Furthermore, the present invention relates to a kit comprising a compound essentially nontoxic to hosts and a DNA comprising an expression unit comprising a DNA encoding a receptor for the compound at the downstream of a promoter functioning specifically in a particular organ, tissue, or cell. For example, "a DNA comprising an expression unit" contained in the kit of the invention is introduced into animal cells to create a transgenic animal, and "a compound essentially nontoxic to a host" that is also contained in the kit of the invention is administered to the transgenic animal at a desired time period, that a particular organ of the transgenic animal can be specifically disrupted depending on the administration period of the compound.

DESCRIPTION OF THE DRAWINGS

FIG. 10 shows the time course of diphtheria toxin concentration in blood after the toxin administration into wild type mice.

BEST MODE FOR IMPLEMENTING THE INVENTION

The following examples are offered by way of illustration and not by way of limitation.

EXAMPLE 1

Purification of Diphtheria Toxin

*Corynebacterium diphtheriae* (strain PW8, freeze-dried) was resuspended in 400 µl of sterilized distilled water, inoculated onto a 1.5% agar plate, and incubated at 37° C. for 24 hours. A single colony was precultured in 2.5 ml of a liquid medium, then in 50 ml, and subsequently cultured in 1 liter of the liquid medium. Each culture was continued at 35° C. for 24 hours with shaking at 250 rpm. Antiseptic gauze was used to cover culture flasks for aeration. To prepare diphtheria toxin, 8 liter of the culture was collected by the above method, and centrifuged at 4000 rpm at 4° C. for 15 min. The supernatant was recovered (the bacteria were removed as much as possible), and phenylmethylsulfonylfluoride (PMSF) was added thereto to 0.1 mM. The supernatant was then concentrated to 500 ml by ultrafiltration (PrepScale Spiral UF Cartridge, Millipore), and ammonium sulfate was added to the concentrate to 40%. The mixture was gently stirred at 4° C. for 30 min, and then centrifuged at 10000 rpm at 4° C. for 30 min. The precipitate was dissolved in buffer A (25 mM $NaH_2PO_4$, 25 mM $Na_2HPO_4$, 150 mM NaCl, and 0.1 mM PMSF, pH 6.5) (500 ml in total), and ammonium sulfate was added again to 40%. The mixture was gently stirred at 4° C. for 30 min and centrifuged at 10000 rpm at 4° C. for 30 min. The precipitate was dissolved in buffer A (100 ml in total). The sample was diluted 20-fold in buffer B (20 mM Tris-HCl, 0.1 mM PMSF, pH 7.5), and the half (1 liter) was loaded onto a DEAE sepharose FF column (2.5 mm diameter×200 mm, Pharmacia), which was previously equilibrated with buffer B. The flow rate was adjusted to 100 ml/hour. The sample was eluted with 500 ml of buffer B containing 0.2 M NaCl at the same flow rate. The other half of the sample (1 liter) was also subjected to the same procedures. Eluted fractions (1 liter) from the above twice DEAR column chromatography were concentrated by ultrafiltration, and the solvent was replaced with PBS(−). Diphtheria toxin was thus obtained at a final concentration of 5.92 mg/ml.

EXAMPLE 2

Plasmid and Transgene Construction

Figure 1:
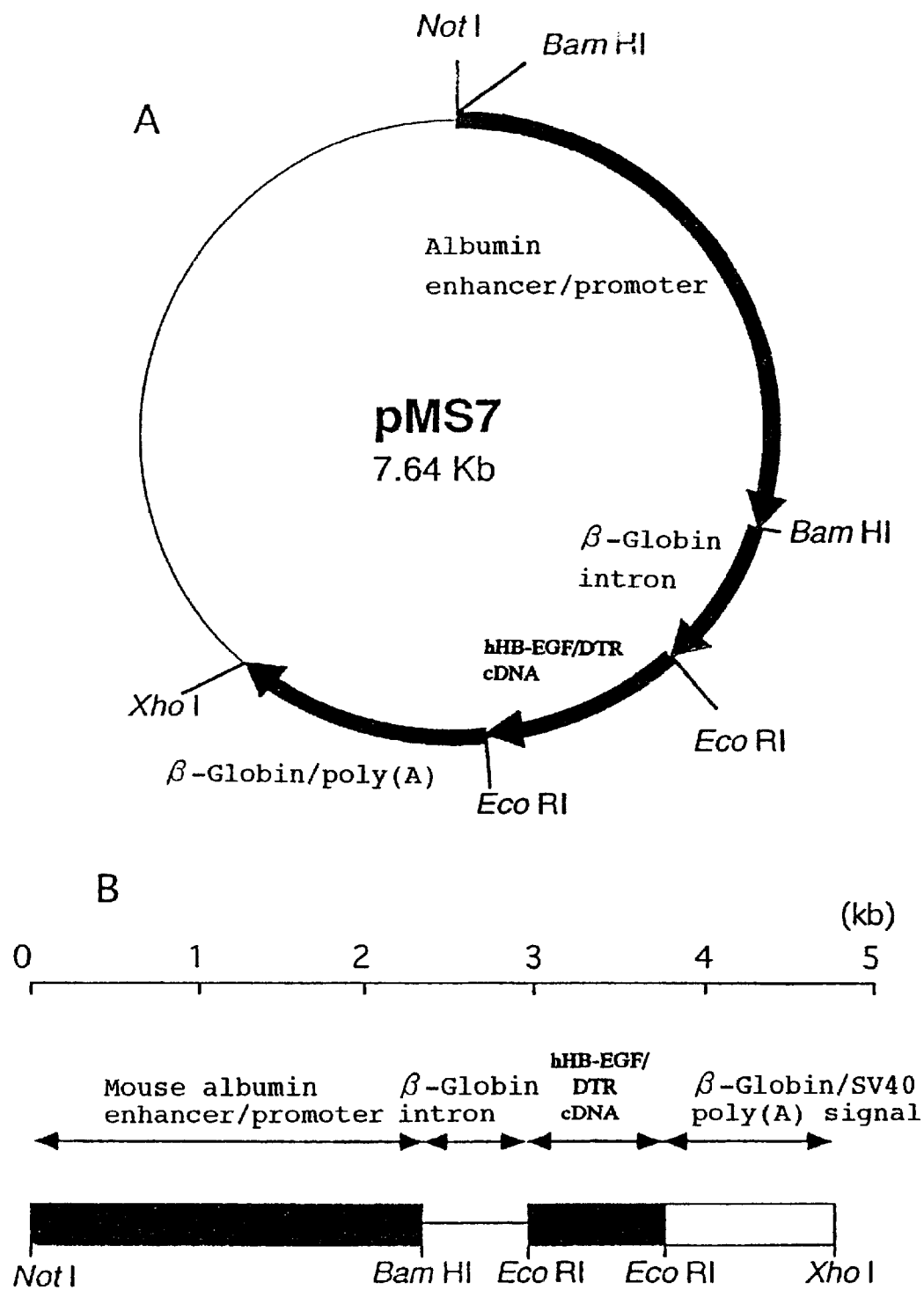
FIG. 1 schematically shows the structures of the plasmid pMS7 (Panel A), and of the transgene introduced into fertilized eggs to create transgenic mice of the present invention (Panel B).

To prepare a transgene, the human HB-EGF cDNA was excised from pRcHBEGF (Iwamoto, R. et al. (1994) EMBO 13, 2322–2330) with BamHI and NotI. Then, the cDNA was blunted with Klenow fragment (DNA polymerase I, Toyobo), an EcoRI linker (Phosphorylated linker, Takara) was added, and the resulting product was inserted into pBluescript(SK−) (the plasmid was named pMS6-1). An EcoRI fragment was excised from the plasmid, and inserted into the EcoRI site of pBstN (provided by Dr. Kazuto Kobayashi, Nara Institute of Science and Technology) to create the plasmid pMS6. Next, the albumin enhancer promoter was excised from p2335A-1 (provided by Dr. Yasushi Kaneda, Cell Technology Center, Osaka University; for preparation of the promoter, see "Gorski, K. et al. (1986) Cell 47, 767–776") with NotI and BamHI, and inserted into the NotI-BamHI site of pMS6, which is located in the 5′ region of the β-globin intron, to create pMS7 (FIG. 1). To remove the vector, pMS7 was treated with NotI and XhoI, separated by electrophoresis on a 0.8% agarose gel, and the transgene was purified using the Prep-A-Gene DNA purification kit (Bio-Rad) or Ultrafree-MC 0.45 mm (Millipore). Transgenes were purified by cesium chloride density gradient centrifugation and used for injection.

EXAMPLE 3

Generation of Transgenic Mice

ICR mice (Clea Japan, Inc.) were used.

(1) Harvesting Fertilized Eggs

Pregnant mare serum gonadotropin (PMSG) (5 IU/mouse; Serotropin, Teikoku Hormone Mfg. Co., Ltd.) was intraperitoneally injected to female mice at 10 o'clock in the morning three days before harvest. Twenty hours before harvest (2 o'clock in the afternoon of the day before), human chorionic gonadotropin (hCG) (5 IU/mouse; Peverogen, Mitsui-zoki) was intraperitoneally injected to the mice, and the mice were caged with male mice for mating. On the next morning, uterine tubes were ablated from female mice, and fertilized eggs were incubated in hyaluronidase medium (1 mg/ml, Sigma) under a stereoscopic microscope to remove cumulus oophorus cells, and washed with PB1 (140 mM NaCl, 2.7 mE KCl, 8 mM $Na_2HPO_4$, 1.5 mM $KH_2PO_4$, 1 mM $CaCl_2$, 0.5 MM $MgCl_2.6H_2O$, 5.6 mM glucose, 9 mM sodium pyruvate, 100 IU/ml penicillin G potassium, and 3 mg/ml bovine serum albumin) medium. The eggs were cultured in a drop of HP medium (88 m NaCl, 4.8 mM KCl, 1.2 mM $KH_2PO_4$, 1.2 mM $MgSO_4.7H_2O$, 1.7 mM calcium lactate, 23 mM $NaHCO_3$, 5.6 mM glucose, 21.6 mM sodium lactate, 0.2 mM sodium pyruvate, 75 μg/ml penicillin G potassium, 50 μg/ml streptomycin sulfate, and 3 mg/ml bovine serum albumin), which was covered with paraffin oil, at 37° C. in 5% $CO_2$ until injection.

(2) Microinjection and Transplantation

DNA (3.2 ng/ml, FIG. 1B) (2 pl; containing 1000 copies of 6 kb DNA according to the assumption: 1 bp=660 Da) was injected to the male pronuclei of fertilized eggs. The eggs were incubated for 1 hour at 37° C. in 5% $CO_2$, and then transplanted into the uterine tubes of pseudopregnant mice. Embryo engineering was carried out and 78 mice were obtained.

(3) PCR Analysis (Identification of Transgenic Mice)

A small piece of an ear from 3-week-old mouse was suspended in 100 μl of PCR buffer (50 mM KCl, 10 mM Tris-HCl (pH 8.0), 1.5 mM $MgCl_2$, 0.1% (w/v) gelatin, 0.45% NP-40, 0.45% Tween-20, and 500 μg/ml proteinase K), incubated at 55° C. for 1 hour, and heated at 95° C. for 5 min to inactivate proteinase K. Five μl of the lysate was used for PCR. Used primers were primers M1 (5'-GCTCTTTCTGGCTGCAGTTC-3' (SEQ ID NO: 1)) and M2 (5'-GCGATTTTCCACTGGGAGGC-3' (SEQ ID NO: 2)), which were specific to the human HB-EGF cDNA. PCR reaction was performed using rTaq DNA polymerase (2U, Takara) by 35 cycles of 94° C. for 1 min, 58° C. for 1 min, and 72° C. for 1 min. The PCR products were separated by electrophoresis on a 0.8% agarose gel. As a result, a single band of approximately 430 bp was detected in six mice out of 78. Thus, the six transgenic mice (Tg16 (male), Tg18 (male), Tg24 (male), Tg51 (male), Tg62 (female), and Tg67 (male)) were obtained. The F1 and F2 progeny of the transgenic mice were used in the following experiments.

(4) Northern Blotting Analysis

To confirm liver-specific expression of the hHB-EGF/DTR gene in the obtained transgenic mice, northern blotting analysis was performed with liver, kidney, spleen, muscle, heart, and lung from Tg16 and Tg24 mice. Specifically, 6- to 8-week-old mice were sacrificed by cervical dislocation, the tissues from the liver, kidney, spleen, skeletal muscle, heart, and lung were excised, and RNA was extracted by the AGPC method (Ran, J. H. et al. (1987) Biochemistry 26, 1617–1625). Fifteen μg of total RNA was separated by electrophoresis on a 1% agarose gel containing 2% formalin, transferred onto a nylon membrane (Hybond-N, Amersham) in 20×SSC, and fixed on the membrane by baking at 80° C. for 2 hours. After 2-hour prehybridization at 42° C. in a buffer (5×SSPE, 50% formamide, 5×Denhardt's, 0.5% SDS, 20 μg/ml calf thymus DNA), the membrane was hybridized overnight at 42° C. with an [α-$^{32}$P]dCTP-labeled HHB-EGF cDNA fragment (783 bp) as a probe. The probe was prepared using the random primer DNA labeling kit ver.2 (Takara). The membrane was washed twice with 6×SSC and 0.1% SDS for 10 min at room temperature, then twice with 2×SSC and 0.1% SDS at room temperature for 10 min, and finally once with 0.1×SSC and 0.1% SDS at 55° C. for 5 min. It was then exposed for 16 hours onto an X-ray film (Kodak) to detect signal. The result shows that the hHB-EGF/DTR gene was not expressed in any tissue except for the liver, confirming the liver-specific expression of the gene (FIG. 2A). Furthermore, northern blotting analysis for the expression level of the hHB-EGF/DTR gene among transgenic lines or within a line indicated that the expression level differs among lines. Among three lines which were used for toxin administration in this experiment, Tg16 showed the highest expression level, whereas Tg67 showed the lowest level, and Tg24 was intermediate (FIG. 2B). However, the expression level among littermates within a line was the same (FIG. 2C).

EXAMPLE 4

In situ Hybridization

To further confirm the liver-specific expression of the hHB-EGF/DTR gene, in situ hybridization was performed on liver sections of Tg16 mice.

(1) Sample Preparation

Livers were excised from 8-week-old mice, immediately frozen in dry ice. Sections of 7 μm thickness were made, pasted down onto a siliconized slideglass, and stored at −80° C. until the use for in situ hybridization.

(2) Probe Preparation

To prepare a probe used for in situ hybridization, the hHB-EGF cDNA was excised from pRcHBEGF (Iwamoto, R. et al. (1994) EMBO 13, 2322–2330) with BglII and SalI and ligated into the BamHI-SalI site of pBluescript(SK−) to generate the plasmid pMS10. pMS10 was digested with XbaI or XhoI and labeled using DIG DNA labeling mixture (Boehringer) to obtain a probe with antisense or sense orientation. T7 polymerase (Promega) was used to prepare antisense strand, and T3 polymerase (Promega) for sense strand.

(3) Pretreatment of the Sample

Sections were fixed in 4% formamide and 0.1 M phosphate buffer (20 mM $NaH_2PO_4$, 80 mM $Na_2HPO_4$, pH 7.4) at room temperature for 20 min, washed twice with 0.1 M phosphate buffer, incubated for 20 min in 0.1 M phosphate buffer containing 0.2 M HCl at room temperature to inactivate endogenous alkaline phosphatase, and then washed again with 0.1 N phosphate buffer twice. The sections were treated with 10 μg/ml proteinase K in 50 mM Tris-HCl and 5 mM EDTA (pH 8.0) at room temperature for 5 min, washed twice with 0.1 M phosphate buffer, fixed in 4% formaldehyde and 0.1 M phosphate buffer (pH 7.4), and acetylated for 10 min in 0.25% anhydrous acetic acid and 0.1 M triethanolamine. The sections were then washed with 0.1 M phosphate buffer, dehydrated in a series of alcohol, defatted in chloroform, and air-dried.

(4) Hybridization

Figure 3:
FIG. 3 shows microscopic photographs showing the result of In situ hybridization that was performed to detect the hHB-EGF/DTR gene expression in liver sections. A and C, Tg16 transgenic mice, in which antisense (A) or sense (C) hHB-EGF gene probe was used; B, wild type.
Figure 3:
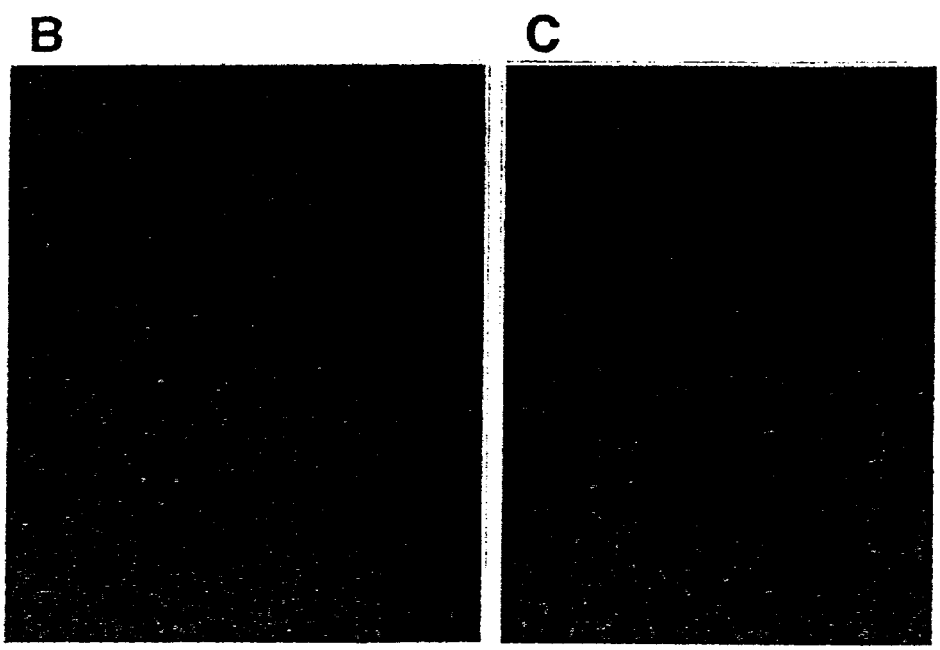

The sections were subjected to prehybridization in hybridization buffer (10% dextran sulfate Na, 20 mM Tris-HCl (pH 8.0), 0.3 M NaCl, 0.2% sarcosyl, 0.2 mg/ml denatured salmon sperm DNA, 500 ng/ml yeast tRNA, 1×Denhardt's solution and 50% formamide) at 37° C. for 60 min in a moistened box. Then, hybridization was performed in hybridization buffer containing a DIG-labeled probe (100 μl/slide) at 55° C. overnight in a moistened box. The sections were washed for 20 min at 60° C. with 4×SSC, and for 30 min at 60° C. with high stringency solution (50% formamide, 2×SSC). Thereafter, the sections were washed three times with RNase buffer (10 mM Tris-HCl (pH7.4), 1 mM EDTA (pH 8.0), and 0.5 M NaCl) at 37° C. for 10 min, incubated at 37° C. for 30 min in RNase buffer containing 2 μg/ml RNase (Sigma), and then washed with RNase buffer at 37° C. for 10 min. The sections were further washed with high stringency solution at 60° C. for 30 min and allowed to develop color using DIG nucleic acid detection kit (Boehringer). The result indicated that the hHB-EGF/DTR gene was expressed in hepatic parenchymal cells and not in other cells (FIG. 3A), confirming hepatic cell-specific expression of the gene. No signal was detected in liver sections from wild type mice (FIG. 3B) as well as in sections treated with sense probes (FIG. 3C).

EXAMPLE 5

Figure 4:
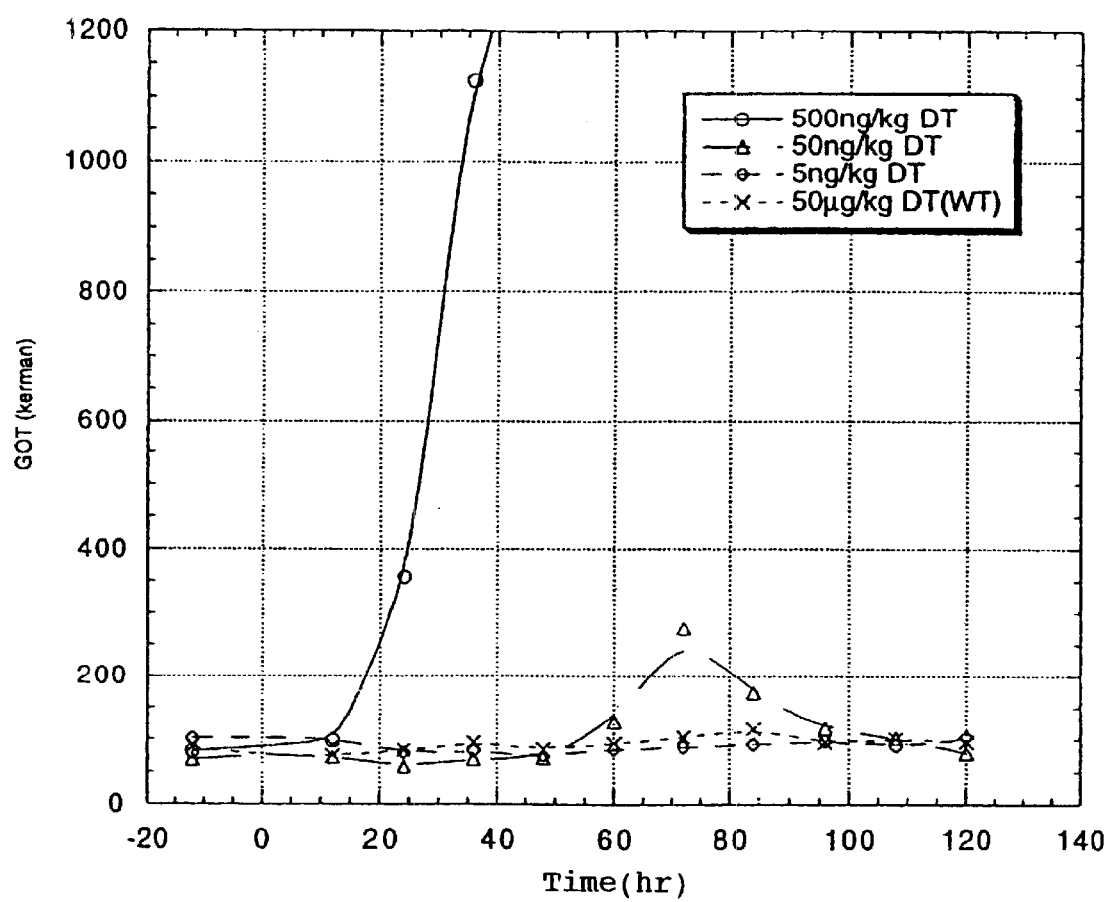
FIG. 4 shows the time course of change in GOT activity in Tg16 transgenic mice after toxin administration.
Figure 5:
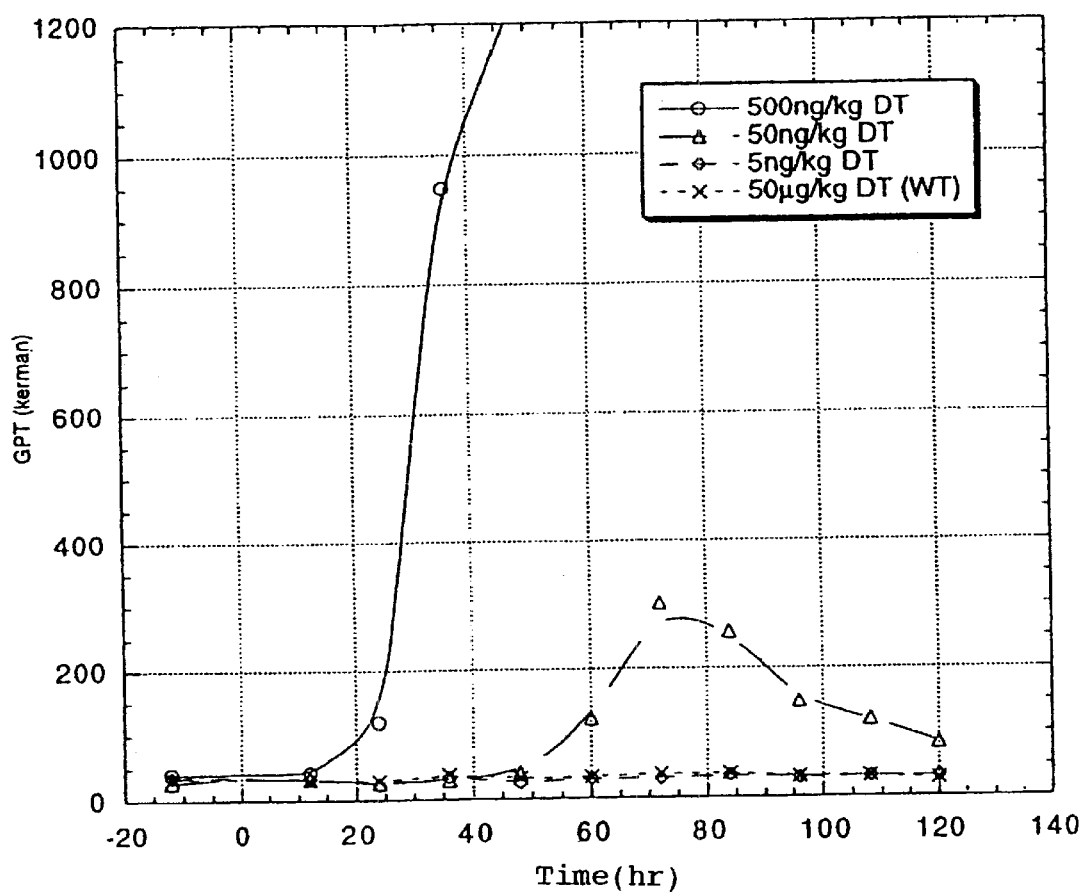
FIG. 5 shows the time course of change in GPT activity in Tg16 transgenic mice after toxin administration.
Figure 6:
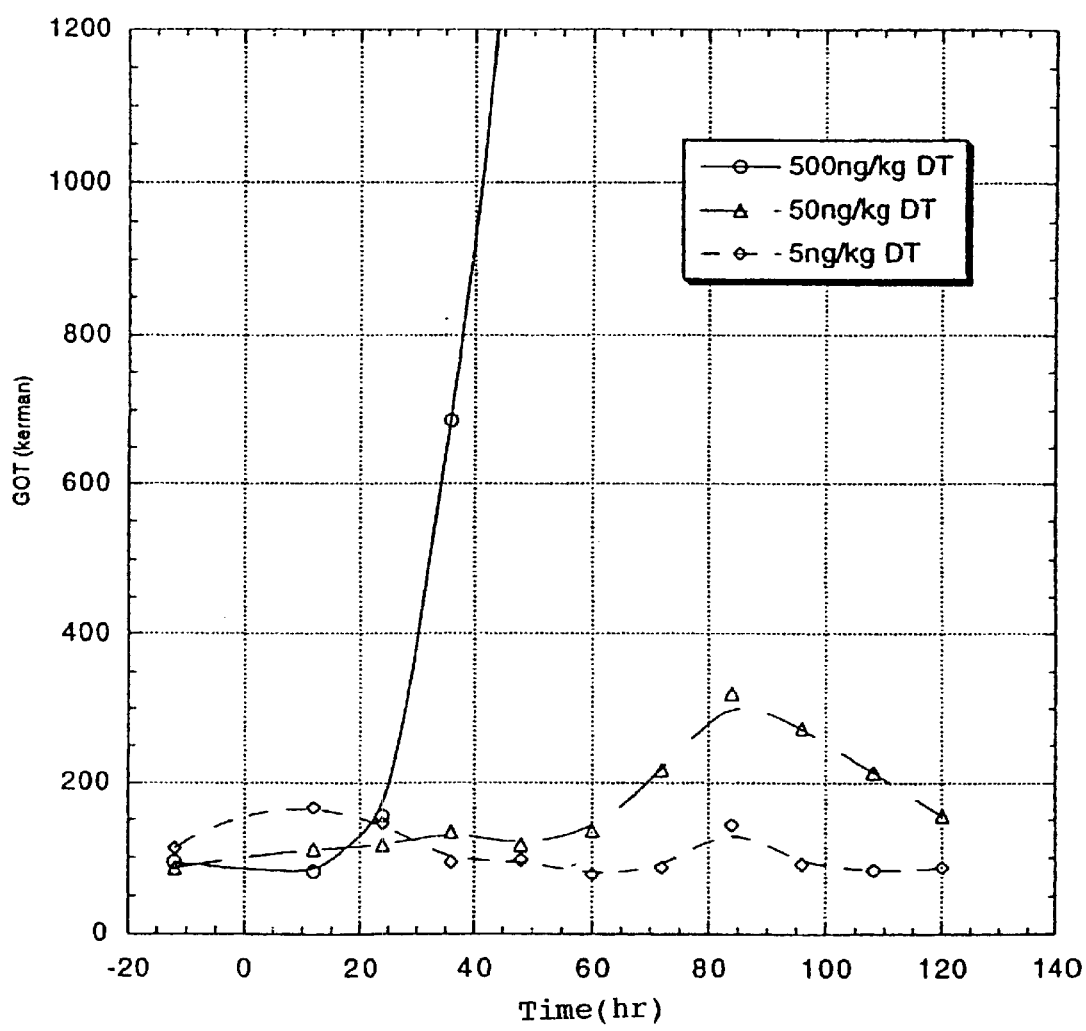
FIG. 6 shows the time course of change in GOT activity in Tg24 transgenic mice after toxin administration.
Figure 7:
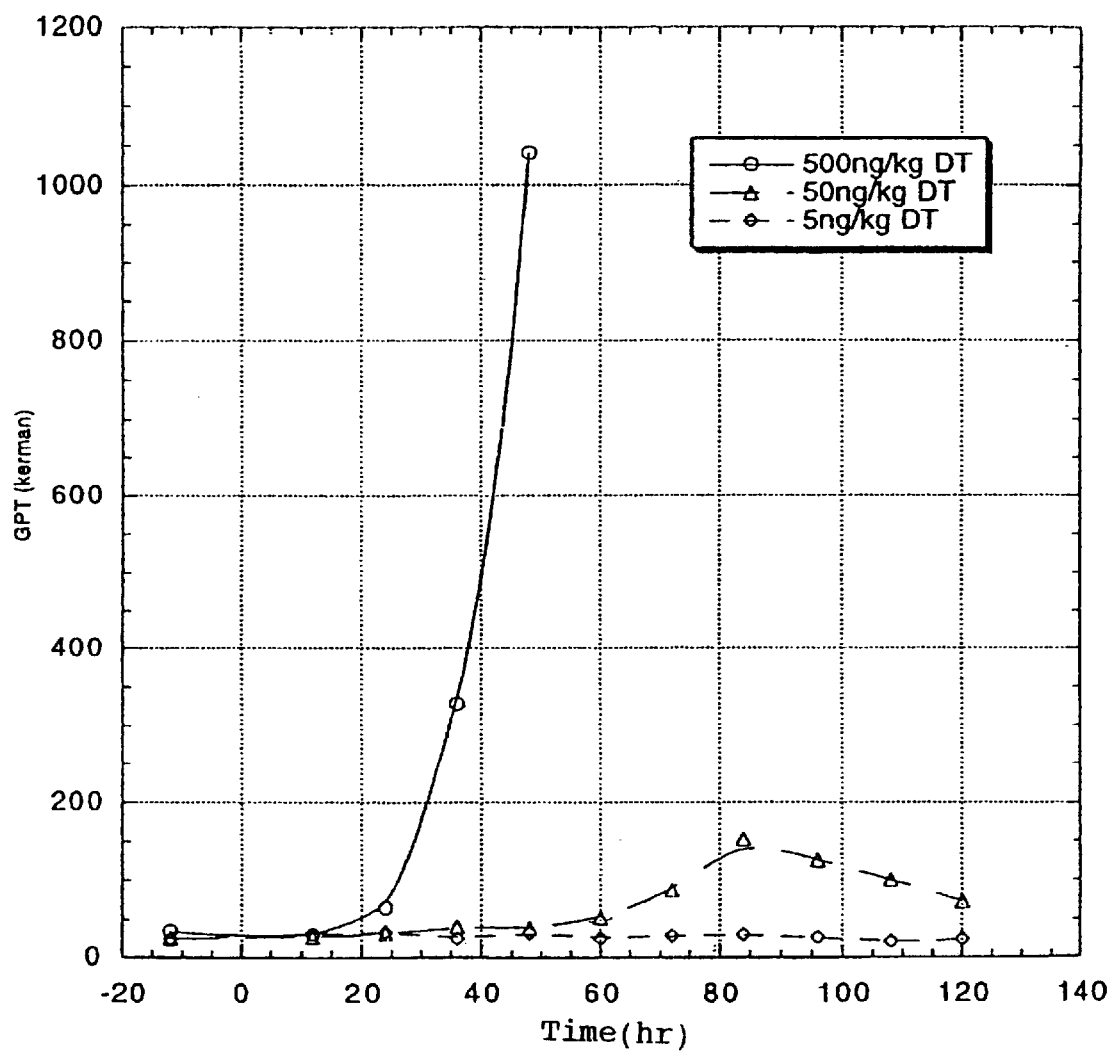
FIG. 7 shows the time course of change in GPT activity in Tg24 transgenic mice after toxin administration.
Figure 8:
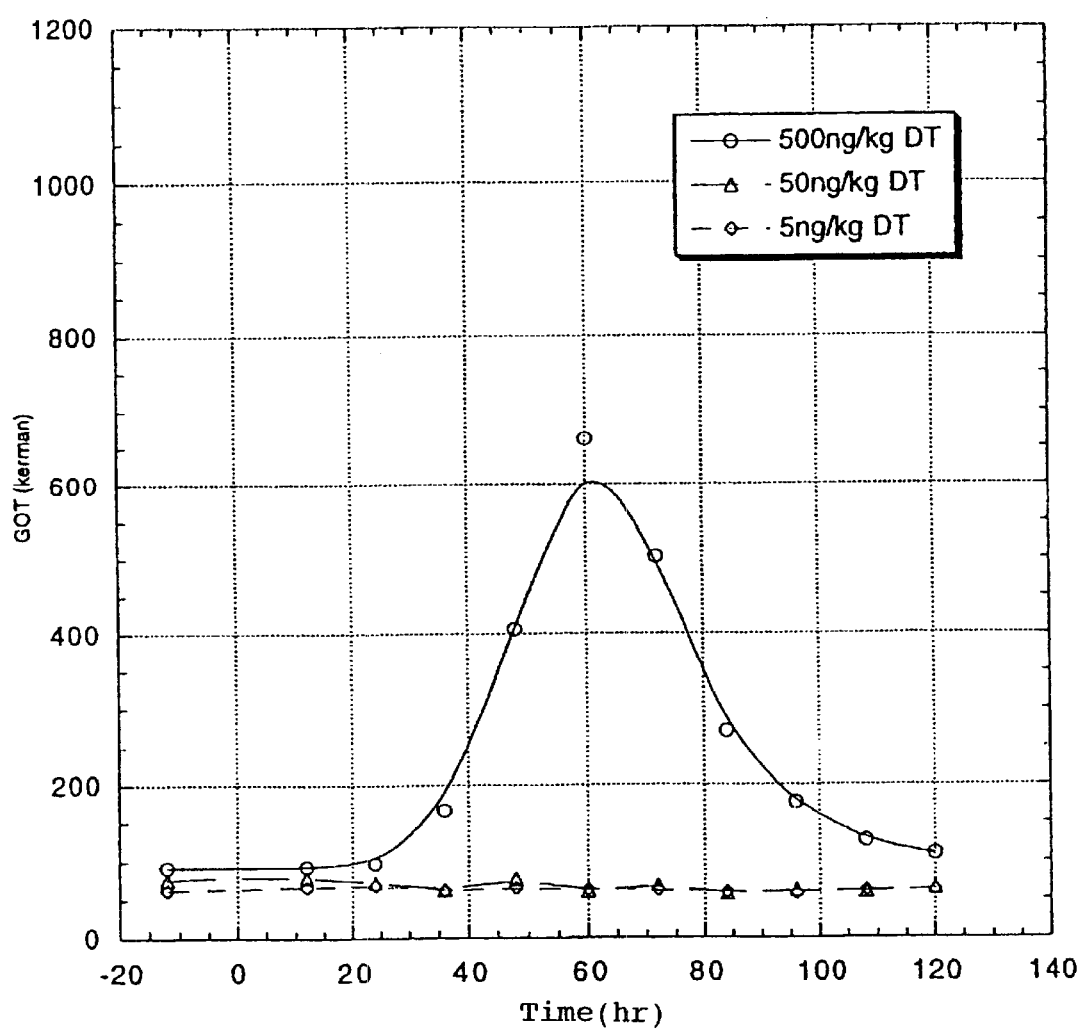
FIG. 8 shows the time course of change in GOT activity in Tg67 transgenic mice after toxin administration.

Measuring Serum Glutamic Oxaloacetic Transaminase (GOT) and Glutamic Pyruvic Transaminase (GPT) Activities The obtained transgenic mice specifically expressed the hHB-EGF/DTR gene in hepatic cells. To examine whether the hepatic cells are specifically disrupted by toxin administration, diphtheria toxin was injected to Tg16, Tg24, an and Tg67 mice and examined for liver disorder. Liver disorder after toxin administration was assessed by measuring serum GOT and GPT activities. Both GOT and GPT are marker enzymes of liver disorder, whose activity are known to be increased in liver disorder. Five different toxin doses, 50 µg, 5 µg, 500 ng, 50 ng, and 5 ng/kg body weight were injected (doses are hereinafter referred to in terms of µg/kg DT or ng/kg DT). For each dose, three mice were examined. Specifically, 100 µl of blood was collected from the tail tops of 6- to 8-week-old mice 12 hours before toxin administration and every 12 hours of 12 to 120 hours after administration. Blood was coagulated at room temperature for 10 min and centrifuged at 10000 rpm at 4° C. for 10 min to obtain serum. GOT and GPT activities were measured using a GOT, GPT activity measuring kit (Transaminase C-test Wako, Wako Pure Chemical). One hundred µl of toxin, diluted appropriately with physiological saline, was injected intramuscularly into the dorsum. The results indicated that administration of 50 µg/kg DT did not alter serum GOT and GPT activities in wild type mice (FIGS. 4 and 5). In contrast, as shown in FIGS. 4 and 5, administration of 500 ng/kg DT increased both GOT and GPT activities in Tg 16 mice after about 12 hours, and then the mice died after about 60 hours. Administration of 50 ng/kg DT increased the both activities after about 50 hours. The activities reached to the maximum after 72 hours and returned to the normal level at about 120 hours. The peak levels of GOT and GPT activities were four and ten times of the normal, respectively. Administration of 5 ng/kg DT did not change either activity. In Tg24 mice, administration of 500 ng/kg DT also increased serum GOT and GPT activities after about 12 hours, and the mice died after about 55 hours (FIGS. 6 and 7). Administration of 50 ng/kg DT increased the activities after about 50 hours. The activities reached to the maximum after 84 hours and returned to the normal level at about 120 hours (FIG. 8). The peak levels of GOT and GPT activities were three and five times of the normal, respectively. Administration of 5 ng/kg DT did not affect the activities. In Tg67 mice, administration of 500 ng/kg DT increased the activities after about 24 hours, the activities reached to the maximum after 60 hours, then returned to the normal level at about 120 hours. The peak levels of GOT and GPT activities were seven and twenty times of the normal, respectively. Administration of 50 and 5 ng/kg DT did not change either activity. In all the three lines, administration of 50 or 5 µg/kg DT increased both activities after about 12 hours, and the mice died between about 30 to 50 hours after administration.

EXAMPLE 6

Tissue Section Preparation

Figure 9:
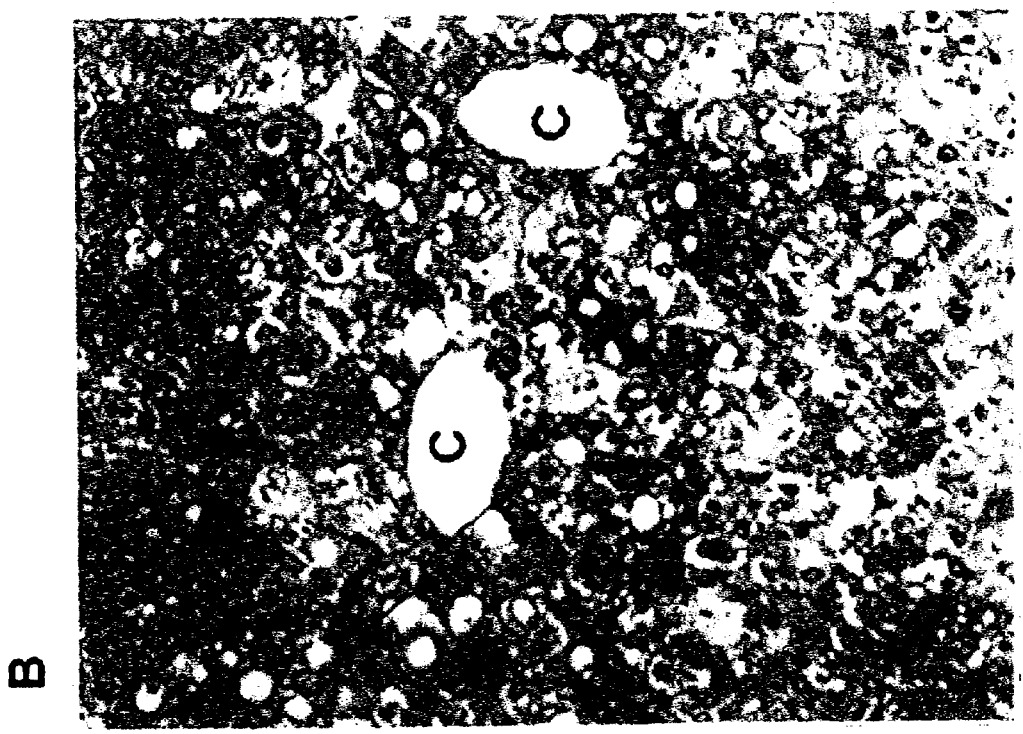
FIG. 9 shows microscopic photographs of sections of livers 35 hours after toxin administration. A, wild type; B, Tg16 transgenic mice. P indicates portal vein and C, central vein of liver.
Figure 9:
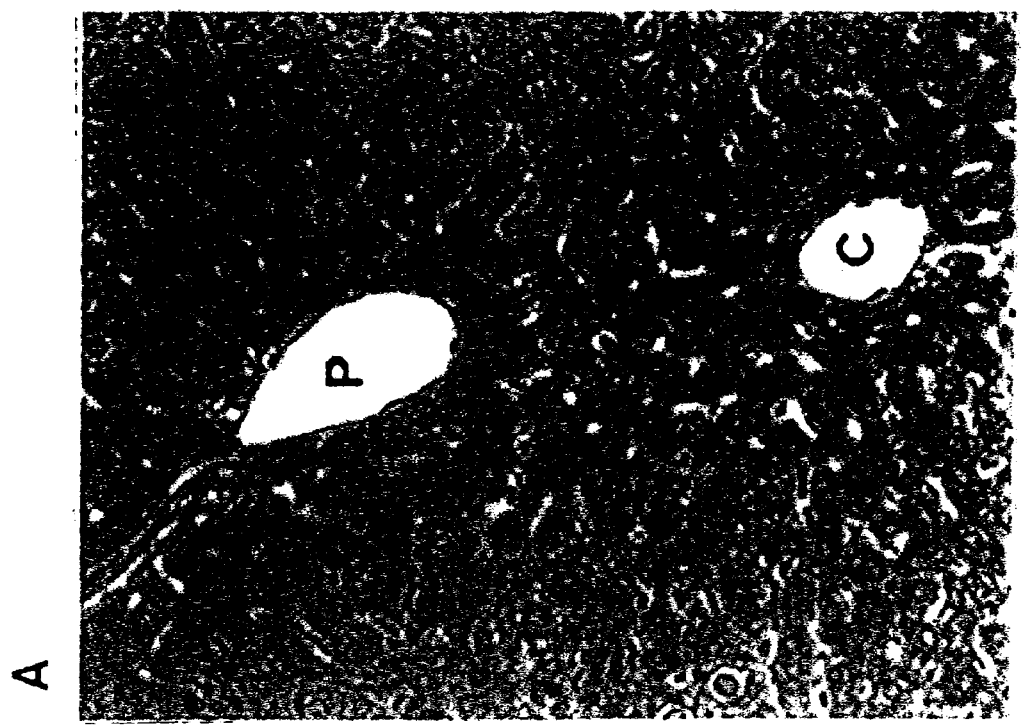

To examine the effect of toxin administration in liver and other tissues, liver, kidney, spleen, heart, and lung were histologically analyzed by hematoxylin eosin (HE) staining. Tg16 mice that died 35 hours after administration of 500 ng/kg DT and wild type mice 35 hours after administration of 50 µg/kg DT were examined. Specifically, tissues were excised immediately after cardiac arrest, fixed in 10% neutral formalin, replaced in PBS(−) after 24 hours, and sectioned in paraffin. The sections were then stained with HE. While wild type liver tissue was histologically normal, Tg16 liver showed necrosis of hepatic cells in broad area and fat accumulation in the hepatic cells. No abnormalities were observed in any other cells composing a liver (FIG. 9). Kidneys, spleens, hearts, and lungs of Tg16 or wild type mice were histologically normal. The results indicated that diphtheria toxin administration affected specifically hepatic cells of transgenic mice, and that the effect was greater in the order of Tg16>Tg24>Tg67, thus revealing a proportionate relationship between the expression level of the hHB-EGF/DTR gene and its effect (FIGS. 2B, and 4 to 8).

EXAMPLE 7

Determination of Diphtheria Toxin Concentration in Blood

The toxin concentration in the body after injection was determined. The toxin was injected to wild type mice injected at a dose of 50 µg/kg, and blood was harvested 1, 2, 4, 7, and 24 hours after injection in the same manner as described above. A predetermined concentration of the blood or toxin was added to Vero cells, a toxin sensitive cell line (ATCC CRL-1586, provided by Dr. Mekata, Institute of Life Science, Kurume University), and diphtheria toxin concentration in blood was determined by comparing the medium effective dose ($ED_{50}$) values for 50% inhibition of protein synthesis. The rate of inhibition of protein synthesis was determined as described below.

Figure 10:
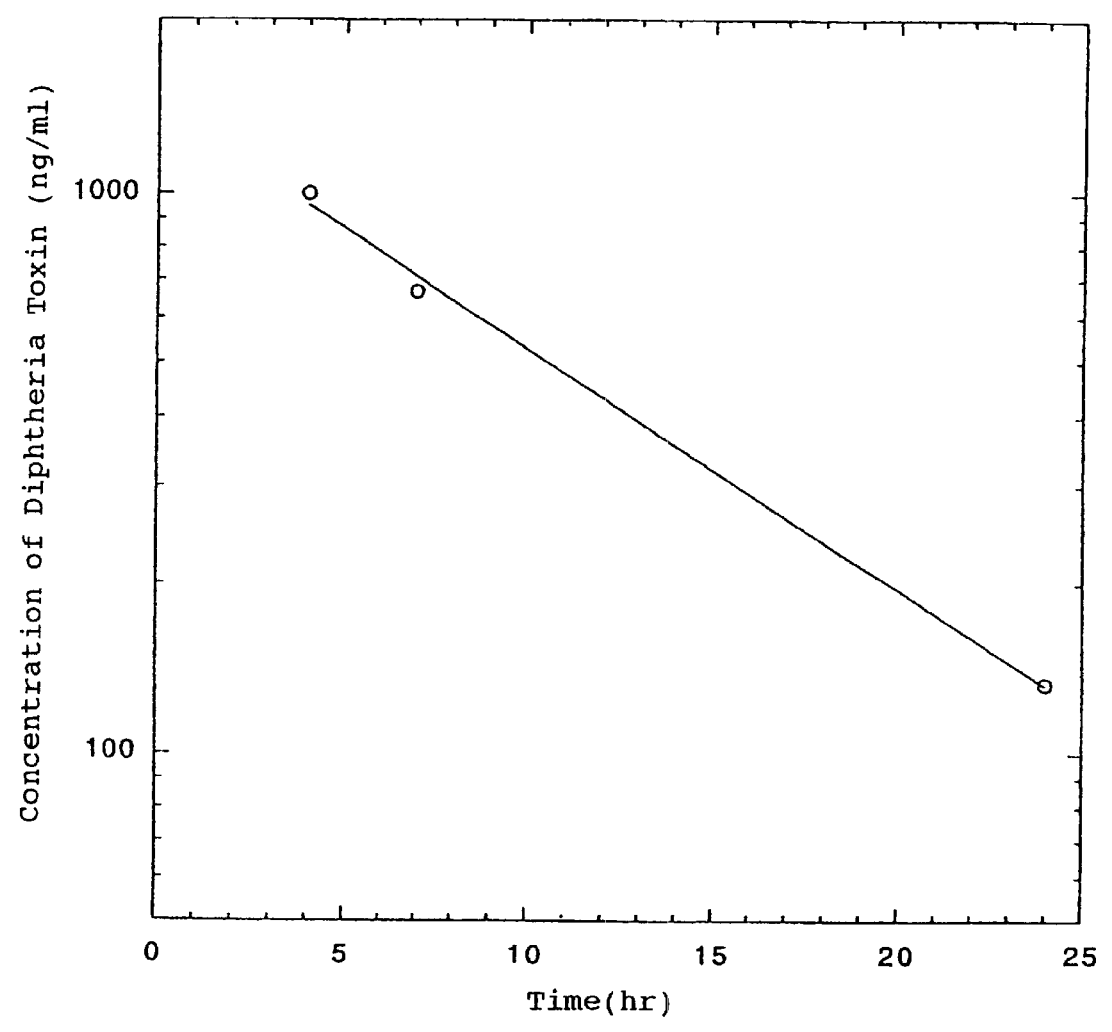

Vero cells were seeded into 24-well plastic dishes (Corning) at $5 \times 10^4$ cells. Five µl of various concentrations of diphtheria toxin (final concentration of 0, $10^{-3}$, $10^{-2}$, $10^{-1}$, 1, and 10 ng/ml) or blood samples of various dilutions (final concentration of 1, $10^{-1}$, $10^{-2}$, $10^{-3}$, $10^{-4}$, and $10^{-5}$%) was added to the culture (500 µl), and the culture was incubated for 6 hours at 37° C. The medium was changed to 200 µl of methionine and cysteine-free medium (Gibco), $^{35}$S-labeled methionine and cysteine (5 µCi/ml) were added to the culture, and then the culture was incubated for 1 hour for uptake of the labeled amino acids. The cells were then washed with PBS(−) and solubilized in 0.1 N NaOH. After 10% trichloroacetic acid was added, the precipitates thus formed were adsorbed onto glassfilters using a 10-well vacuum glassfilter folder, and the radioactivity was measured using a liquid scintillation counter (Beckman) (Kohno, K. et al. (1985) Somatic Cell Mol. Genet. 11, 421–431; Umata, T. et al. (1990) J. Biol. Chem. 265, 21940–21945). As shown in FIG. 10, the diphtheria toxin concentration in blood reached to the maximal level (1 µg/ml) 2 to 4 hours after injection and remained at 100 ng/ml after 24 hours (FIG. 10).

EXAMPLE 8

Effect of hHB-EGF Expression

Figure 2:
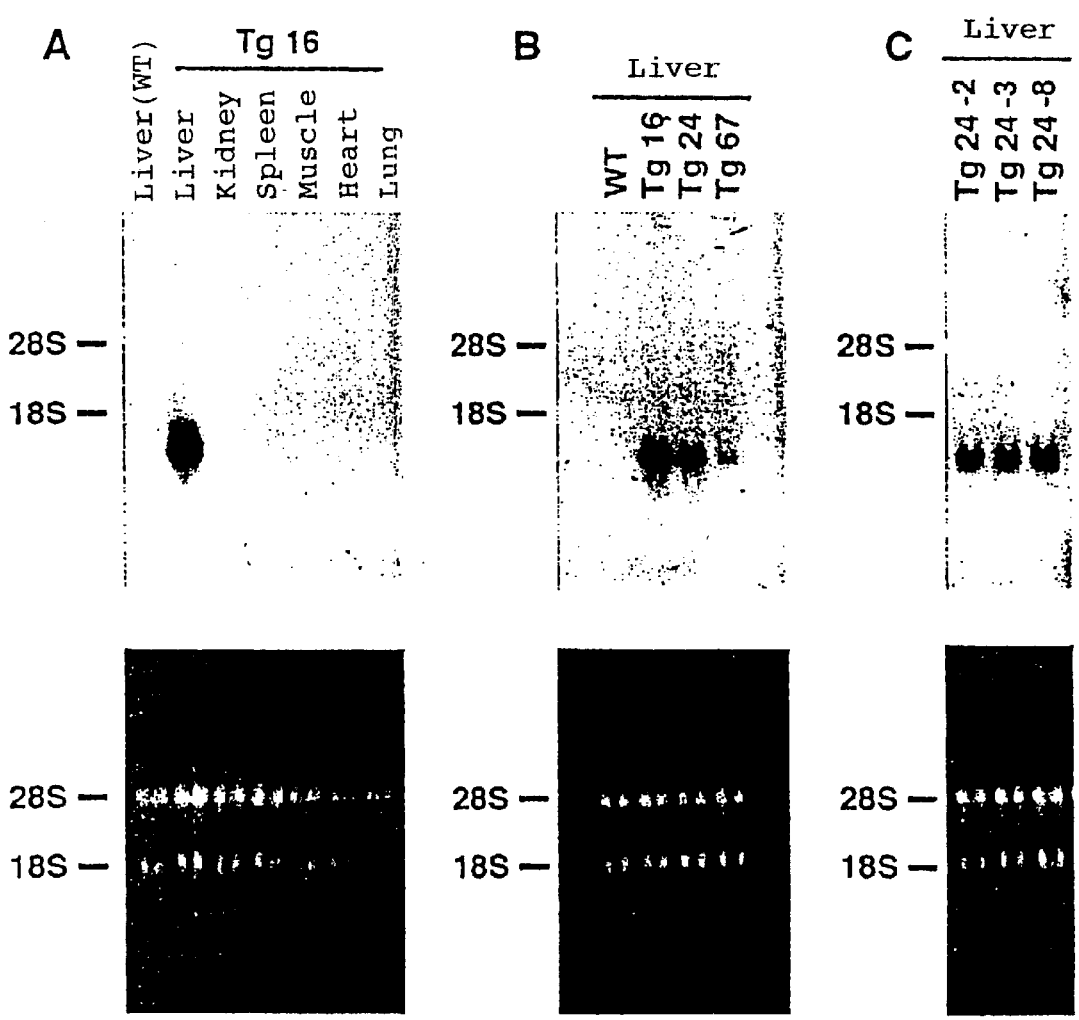
FIG. 2 shows an image on an x-ray film showing the result of northern blotting analysis performed to detect the expression of the hHB-EGF/DTR gene in various organs of a transgenic mouse (Tg 16) (Panel A, upper part), in various lines of transgenic mice (Panel B, upper), or within the Tg24 line (Panel C, upper). The lower part of each panel shows an image of electrophoresis of total RNA from organs corresponding to the upper.

The hHB-EGF gene introduced into mouse embryo functions not only as a growth factor but also as a receptor of diphtheria toxin. Thus, the transgenic mice was expected to have disorder in liver morphogenesis. However, while the hHB-EGF gene was overexpressed in the transgenic mice as shown in FIG. 2, there was no morphological or histological abnormality in their livers. In addition, there was no difference in liver weight relative to body weight between wild type and Tg 16 mice; both had a liver weight about 6 to 7% of the body weight.

INDUSTRIAL APPLICABILITY

The present invention provides a method for selectively disrupting a particular organ or the like target, and thus overcome the problem in surgical ablation that it is impossible to ablate only target cells efficiently when the target cells exist in the body diffusely. The invention also enables disrupting an organ or the like target depending on the administration period of a compound. When a target organ is essentially required for development, the conventional methods utilizing toxin expression result in death of the individual at embryo stage, which makes it impossible to analyze the animal after birth. In contrast, the present invention is free from such a problem. The present invention provides a method of knockout of a cell in a spatiotemporally controllable manner.

What is claimed is:

1. A transgenic mouse whose genome comprises an expression unit including a gene encoding the precursor of the human heparin-binding EGF-like growth factor (hHB-EGF)/diphtheria toxin receptor (DTR) linked to an albumin enhancer/promoter, wherein an administration of diphtheria toxin to the mouse results in the disruption of liver cells.

2. A method for specifically disrupting a liver cell at a particular period in the mouse of claim 1, wherein said method comprises administering a diphtheria toxin to the mouse at said particular period.

* * * * *

UNITED STATES PATENT AND TRADEMARK OFFICE
CERTIFICATE OF CORRECTION

PATENT NO. : 6,576,813 B2
DATED : June 10, 2003
INVENTOR(S) : Kenji Kohno

It is certified that error appears in the above-identified patent and that said Letters Patent is hereby corrected as shown below:

Title page,
Item [56], References Cited, OTHER PUBLICATIONS,
"Walther et al." reference, replace "theapy" with -- therapy --
Item [57], ABSTRACT, replace "hapatic cells, diphtehria" with -- hepatic cells, diptheria --.

Column 1,
Line 29, replace "Nature 3664" with -- Nature 366, --.

Column 4,
Line 60, replace "minituarized" with -- miniaturized --.

Column 5,
Line 23, replace "in situ" with -- situ --.

Column 6,
Line 17, replace "DEAR" with -- DEAE --; and
Line 65, replace "2.7 mE" with -- 2.7 mM --.

Column 7,
Line 2, replace "88 m" with -- 88 mM --;
Line 41, replace "Ran" with -- Han --; and
Line 49, replace "HHB-EGF" with -- hHB-EGF --.

Column 8,
Line 29, replace "0.1 N" with -- 0.1 M --

UNITED STATES PATENT AND TRADEMARK OFFICE
CERTIFICATE OF CORRECTION

PATENT NO. : 6,576,813 B2
DATED : June 10, 2003
INVENTOR(S) : Kenji Kohno

It is certified that error appears in the above-identified patent and that said Letters Patent is hereby corrected as shown below:

Column 9,
Line 3, replace "an and" with -- and --.

Signed and Sealed this

First Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,576,813 B2
DATED : June 10, 2003
INVENTOR(S) : Kenji Kohno

It is certified that error appears in the above-identified patent and that said Letters Patent is hereby corrected as shown below:

Title page,
Item [56], References Cited, OTHER PUBLICATIONS, "Walther et al." reference, replace "theapy" with -- therapy --.
Item [57], ABSTRACT,
Line 6, replace "hapatic cells, diphtehria" with -- hepatic cells, diphtheria --.

Column 1,
Line 29, replace "Nature 3664" with -- Nature 366, --.

Column 4,
Line 60, replace "minituarized" with -- miniaturized --.

Column 5,
Line 23, replace "In situ" with -- in situ --.

Column 6,
Line 17, replace "DEAR" with -- DEAE --; and
Line 65, replace "2.7 mE" with -- 2.7 mM --.

Column 7,
Line 2, replace "88 m" with -- 88 mM --;
Line 41, replace "Ran" with -- Han --; and
Line 49, replace "HHB-EGF" with -- hHB-EGF --.

Column 8,
Line 29, replace "0.1 N" with -- 0.1 M --.

UNITED STATES PATENT AND TRADEMARK OFFICE
CERTIFICATE OF CORRECTION

PATENT NO. : 6,576,813 B2
DATED : June 10, 2003
INVENTOR(S) : Kenji Kohno

It is certified that error appears in the above-identified patent and that said Letters Patent is hereby corrected as shown below:

<u>Column 9,</u>
Line 3, replace "an and" with -- and --.

Signed and Sealed this

Nineteenth Day of July, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gctctttctg gctgcagttc                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gcgattttcc actgggaggc                    20